US011484615B2

(12) United States Patent
Coulston et al.

(10) Patent No.: US 11,484,615 B2
(45) Date of Patent: *Nov. 1, 2022

(54) CUCURBITURIL COMPOSITIONS AND THEIR USE

(71) Applicant: AQDOT LIMITED, Cambridge (GB)

(72) Inventors: Roger Coulston, Cambridge (GB); Alexander Tanner, Cambridge (GB); Jose Martinez-Santiago, Cambridge (GB)

(73) Assignee: AQDOT LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/076,848

(22) PCT Filed: Feb. 15, 2017

(86) PCT No.: PCT/GB2017/050394
§ 371 (c)(1),
(2) Date: Aug. 9, 2018

(87) PCT Pub. No.: WO2017/141029
PCT Pub. Date: Aug. 24, 2017

(65) Prior Publication Data
US 2018/0339078 A1    Nov. 29, 2018

(30) Foreign Application Priority Data

Feb. 15, 2016  (GB) ..................................... 1602665
Dec. 22, 2016  (GB) ..................................... 1621959

(51) Int. Cl.
*A61L 9/01*     (2006.01)
*A61L 2/16*     (2006.01)
*A61L 9/04*     (2006.01)

(52) U.S. Cl.
CPC ........ *A61L 9/01* (2013.01); *A61L 2/16* (2013.01); *A61L 9/04* (2013.01); *A61L 2209/14* (2013.01); *A61L 2209/21* (2013.01)

(58) Field of Classification Search
CPC .......... A61L 9/01; A61L 2209/21; A61L 2/16; A61L 9/014
See application file for complete search history.

(56) References Cited

U.S. PATENT DOCUMENTS

| | | | |
|---|---|---|---|
| 5,942,217 A | 8/1999 | Woo et al. | |
| 6,869,466 B2 | 3/2005 | Day et al. | |
| 7,208,464 B2 | 4/2007 | Heltovics et al. | |
| 7,919,452 B2 | 4/2011 | Malton et al. | |
| 10,695,277 B2 * | 6/2020 | Coulston .................. | A61L 9/01 |
| 2002/0133003 A1 | 9/2002 | Kim et al. | |
| 2003/0068295 A1 * | 4/2003 | Rohde ....................... | A61L 9/01 |
| | | | 424/76.1 |
| 2003/0140787 A1 | 7/2003 | Day et al. | |
| 2005/0008531 A1 * | 1/2005 | Parkhurst .................. | A61L 9/01 |
| | | | 422/4 |
| 2009/0234039 A1 | 9/2009 | Schutte et al. | |
| 2015/0314027 A1 | 11/2015 | Kim et al. | |

FOREIGN PATENT DOCUMENTS

| | | | | |
|---|---|---|---|---|
| GB | 2547281 A | 8/2017 | | |
| KR | 10-2006-0088926 A | 8/2006 | | |
| KR | 10-2015-0060011 A | 6/2015 | | |
| WO | 2014/077640 A1 | 5/2014 | | |
| WO | 2014/077641 A1 | 5/2014 | | |
| WO | 2014/077642 A1 | 5/2014 | | |
| WO | WO-2014077641 A1 * | 5/2014 | ............. | A61L 9/014 |
| WO | WO-2014077642 A1 * | 5/2014 | ............. | A61L 9/014 |
| WO | 2014/114345 A1 | 7/2014 | | |

OTHER PUBLICATIONS

O'Connell, Why does fish smell?, The Irish Times, Apr. 17, 2012, printed from https://www.irishtimes.com/news/health/why-does-fish-smell-1.503246, 2 pages.*
Sato et al., Analysis of Malodorous Substances of Human Feces, Journal of Health Science, 2002, 48(2), pp. 179-185.*
Johnson et al., Aerosol Generation by Modern Flush Toilets, Aerosol Science and Technology, (2013), 47:9, 1047-1057.*
Yokoo et al., Amount of Moisture Produced Inside Bathroom an Appurtenant Changing Room, 2007, printed from https://www.researchgate.net/publication/237557058_AMOUNT_OF_MOISTURE_PRODUCED_INSIDE_BATHROOM_AND_APPURTENANT_CHANGING_ROOM, 9 pages.*
True Energy Solutions (What you need to know about bath fans and humidity, Oct. 2015, https://www.trueenergysolutions.com/about-us/news-and-events/19262-what-you-need-to-know-about-bath-fans-and-humidity.html) (Year: 2015).*
Oct. 22, 2019 Office Action issued in U.S. Appl. No. 16/077,852.
Jan. 17, 2020 Office Action issued in U.S. Appl. No. 16/077,852.
Apr. 21, 2017 International Search Report issued in International Patent Application No. PCT/GB2017/050394.
Apr. 21, 2017 Written Opinion issued in International Patent Application No. PCT/GB2017/050394.
Lagona, Jason, et al. "The Cucurbit[n]uril Family". Angewandte Chemie International Edition, vol. 44, iss. 31, pp. 4844-4870, 2005.
Del Valle, E.M. Martin, "Cyclodextrins and their uses: a review". Process Biochemistry, 2003, doi:10.1016/S0032-9592(03)00258-9.
Liu, Chuanjun, et al. "Visualization of controlled fragrance release from cyclodextrin inclusion complexes by fluorescence imaging". Flavour and Fragrance Journal, vol. 29, pp. 356-363, 2014.
Kim, Kimoon, et al. "Functionalized cucurbiturils and their applications". Chemical Society Reviews, vol. 36, pp. 267-279, 2007.
Apr. 7, 2017 International Search Report issued in International Patent Application No. PCT/GB2017/050395.

(Continued)

*Primary Examiner* — Mark V Stevens
(74) *Attorney, Agent, or Firm* — Oliff PLC

(57) ABSTRACT

The use of compositions including two or more cucurbiturils in counteracting malodour in a moist environment. The two or more cucurbiturils are selected from CB[5], CB [6], CB [7] and CB[8]. Also provided is a method for counteracting malodour in a moist environment, including application of a composition including a mixture of two or more cucurbiturils selected from CB[5], CB[6], CB[7] and CB[8].

17 Claims, No Drawings

(56) References Cited

OTHER PUBLICATIONS

Apr. 7, 2017 Written Opinion issued in International Patent Application No. PCT/GB2017/050395.
Apr. 1, 2020 Notice of Allowance Issued in U.S. Appl. No. 16/077,852.
Jan. 2, 2020 Office Action issued in European Patent Application No. 17706858.2.
J.R. Masoner et al., "Water Quality and Possible Sources of Nitrate in the Cimarron Terrace Aquifer, Oklahoma, 2003," USGS Scientific Investigations Report 2004-5221, 2004, pp. 1-60, url: https://pubs.usgs.gov/sir/2004/5221/pdf/sir04-5221.pdf.
S. Widder et al., "3-Mercapto-2-methylpentan-1-ol, a New Powerful Aroma Compound," Journal of Agricultural and Food Chemistry, American Chemical Society, vol. 48, No. 2, Feb. 2000, pp. 418-423.
"Relative humidity" Wikipedia, Edited Nov. 2018, Retrieved Jul. 2019, url: https://en.wikipedia.org/wiki/Relative_humidity.
"New Cosmos Electric (COSMOS) portable model smell sensor mini XP-329m," Rakuten Global Market, Retrieved Dec. 2019, url: https://global.rakuten.com/en/store/douguyasan/item/cosm-xp-329m/.
Jack Dean Frus, "Chemical oxygen demand as a numerical measure of odor level," Retrospective These and Dissertations, Iowa State University Digital Repository, 1969, pp. 1-101.
Omoto et al., "Recent Changes in Trends of Humidity of Japanese Cities". J. Japan Soc. Hydrol & Water Resour. vol. 7, No. 2, pp. 106-113, 1994 (English Abstract provided).

* cited by examiner

CUCURBITURIL COMPOSITIONS AND THEIR USE

FIELD OF THE INVENTION

This invention relates to use of compositions comprising cucurbiturils in counteracting malodour. More particularly, the invention relates to use of compositions comprising a mixture of cucurbiturils having a distribution of sizes in counteracting malodour. The invention relates also to the application of such compositions in counteracting complex malodours under moist conditions.

BACKGROUND

Malodours are often complex mixtures of different molecules having diverse chemistries and smells. The smell of malodour may be pungent and even minute amounts of such molecules can create uncomfortable impressions to consumers. Therefore, many strategies have been proposed to counteract malodours. Preventive methods involve killing the bacteria that are responsible for the generation of malodours or inhibiting their growth, either by applying biocides, biostatic agents or controlling the microclimatic conditions in the locus where bacteria proliferate. These methods are used for example in the axilla or other part of the human or pet body. Eliminative methods involve using chemically reactive molecules that bind to the malodour and neutralize it; oxidation (burning) and ionization belong to eliminative methods. The disadvantage of all of these methods is that they involve agents that are not chemically or biologically inert, environmentally neutral. In particular the use of biocides and reactive chemicals is subject to sanitary concerns. The by-products of ionization and combustion may also be toxic and undesirable.

Alternatively, perfume and perfumery can be used to mask or combine the malodour in a way that the perception of the malodour by the consumer is reduced. However, complex malodours are difficult to mitigate by using such sensory methods, because of the diversity of smells involved.

Malodour suppression methods involve the use of absorbents and adsorbents. These materials are environmentally friendly and in most cases have no noticeable odour. Malodour molecules are trapped in the pores of these materials and, therefore, their vapour pressure is depressed. However, these materials are generally not selective to malodour and may also bind desirable fragrance molecules. On the other hand water vapours, such as those present in moist conditions, for example above 50% relative humidity, may displace the malodour which is then released back into the air.

Guest molecules are a special class of absorbents, characterized in that each molecule has a well-defined cavity instead of a distribution of pores.

Host-guest complexes have been used in the field of perfumery and for malodour counteracting for some time. For example, U.S. Pat. No. 5,942,217 describes the use of an aqueous solution of cyclodextrin, more generally referred to as cyclic oligosaccharides, for neutralizing malodour. Absorption of the malodour molecule in the cyclodextrin cavity results in efficient mitigation of malodour. The malodour binding process occurs during drying, and low molecular weight polyols can be added to the composition to enhance the formation of cyclodextrin inclusion complexes, especially in the case where the malodour molecule is too small to form a stable inclusion complex.

The action of cyclodextrin on the perception of both malodours and perfumes depends strongly on the activity of water in the system. This reflects complex equilibria involving water, fragrance and malodour inclusion in the cyclodextrin cavity. Hence, the apparent host-guest binding constant may vary for both fragrances and malodours, depending on the concentration of water in the system. The poor predictability of such, essentially non-equilibrium effects, is a source of recurring difficulties for the perfumer. The poor selectivity of cyclodextrin binding and release with respect to fragrances and malodours is a disadvantage. Although this effect can be beneficial in the context of the controlled release of a desirable odour, it becomes very unsatisfactory if the guest molecule released is a malodour.

Another disadvantage of cyclodextrins is the tendency of these carbohydrate-derived materials to become sticky at low water levels or with decreasing water activity. This can lead to, for example, an undesirable "tacky" feeling on the skin. Finally, as is usually the case with aqueous carbohydrate solutions, aqueous cyclodextrin solutions must be preserved against micro-organism invasion using significant amounts of preservatives.

In view of the disadvantages associated with cyclodextrin, alternative host-guest systems are desirable which overcome these problems. In U.S. Pat. No. 6,869,466, a method is described to bind a gas or a volatile molecule to a cucurbituril to form an inclusion complex as well as steps for releasing at least some of the bound gas or volatile compounds. Trapping a malodorous compound is mentioned as an example of application. The formation of the host-guest complex is described as occurring in both dry state, for example with the cucurbituril host molecules adsorbed or supported on a solid surface or dissolved or dispersed in a liquid, for example water.

WO2014077642 describes a composition comprising cucurbit[7]uril for use in odour removal and provides some evidence that odour is complexed with the cucurbituril.

Although cucurbituril host-guest complexes overcome many of the disadvantages associated with cyclodextrin complexes, there is a need for cucurbituril host-guest complexes that provide improved odour control in moist systems.

SUMMARY OF THE INVENTION

The present invention generally provides for use of a composition comprising a mixture of at least two different cucurbiturils selected from CB[5], CB[6], CB[7] and CB[8] under moist conditions in counteracting complex malodours.

In one aspect, there is provided use of a composition comprising a mixture of two or more different sized cucurbiturils selected from CB[5], CB[6], CB[7] and CB[8], for counteracting malodour in a moist environment.

In a second aspect, there is provided a method of counteracting malodour in a moist environment, by applying a composition comprising a mixture of two or more different sized cucurbiturils selected from CB[5], CB[6], CB[7] and CB[8].

In one embodiment, the composition comprises CB[6] and CB[7]. In another embodiment, the composition comprises CB[6], CB[7] and CB[8]. In another embodiment, the composition comprises CB[5], CB[6], CB[7] and CB[8].

The cucurbiturils are present in the composition as a mixture of at least two different sized cucurbituril selected from CB[5], CB[6], CB[7] and CB[8]. Where the cucurbiturils are referred to as cucurbit[n]uril, the composition comprises a mixture of different sized cucurbit[n]urils, wherein n is an integer from 4 to 20 and wherein the mixture comprises at least two different cucurbiturils selected from the group consisting of CB[5], CB[6], CB[7] and CB[8].

In one embodiment, the moist conditions have a relative humidity higher than about 35%.

These and other aspects and embodiments of the invention are described in further detail below.

DETAILED DESCRIPTION OF THE INVENTION

The present inventors have found that a mixture of cucurbituril compounds having a distribution of sizes is especially efficient for suppressing malodours consisting of two or more malodour components, even if these components have a low molecular weight, are volatile or have a particularly pungent smell In particular, the action of malodour suppression can be performed under moist conditions.

The terms "moist" and "wet" or "humid" are used interchangeably throughout. The terms "conditions", "environment" and "system" in relation to the terms "moist", "wet" and "humid" are also used interchangeably throughout.

In the context of the present invention, moist conditions, also referred to as humid conditions, mean that the air at the location where the cucurbituril are used, for example, where the cucurbituril composition is applied, has a relative humidity higher than 40%, still more particularly higher than about 50%, still more particularly higher than about 60%, still more particularly higher than about 70%, still more particularly higher than about 80%, still more particularly higher than about 90% under ambient temperature, for example at about 25° C. About means, ±1%, or ±1° C.

The relative humidity is expressed as a percentage by volume of the maximum amount of moisture the air can hold at a given temperature between 0° C. and 100° C. More accurately, the relative humidity is defined as the ratio of the effective partial vapour pressure under the conditions of application of the cucurbituril compounds to that of the vapour pressure of water at equilibrium, also referred to as "saturation", at same temperature.

Typical moist environments that are concerned by the present invention are, for example, a bathroom, a shower cabin, a toilet bowl, a wash machine, a dish wash machine, a kitchen wash area, a kitchen ventilation hood, a shoe interior, an axilla, a denture, a mammalian body cavity, mammalian skin, a garbage bag, a toilet bowl, a cellar, a sport cloth, a wet carpet, pet litter, a sewage drain, a gutter system, and the like.

In one embodiment, the environment has a relative humidity of 40%, under ambient temperature.

In another embodiment, the environment has a relative humidity of 88%, under ambient temperature.

In a particular embodiment, the environment has a relative humidity of 100%, under ambient temperature.

In one embodiment, the mixture of cucurbiturils comprises CB[5], CB[6], CB[7] and CB[8] curcurbituils, wherein CB[5] can form a complex with small malodour molecules.

Cucurbituril

The present invention provides the use of a cucurbituril to form a complex with a malodour molecule.

Cucurbituril is a member of the cavitand family, and the general cucurbituril structure is based on the cyclic arrangement of glycoluril subunits linked by methylene bridges.

The preparation and purification of cucurbituril compounds is well described in the art. For example, Lagona et al. review the synthesis and properties of cucurbituril compounds, including derivatives, analogues and congener within the cucurbituril family.

For example, cucurbit[8]uril (CB[8]; CAS 259886-51-6) is a barrel shaped container molecule which has eight repeat glycoluril units and an internal cavity volume of 479A$^3$ (see structure below). CB[8] is readily synthesised using standard techniques and is available commercially (e.g. Sigma-Aldrich, Missouri USA).

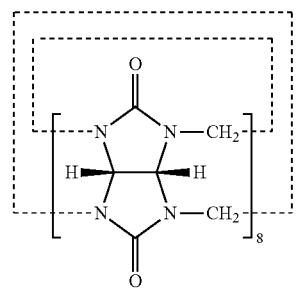

The cucurbituril is present as a mixture of two or more CB[n], wherein the mixture comprises at least two different cucurbiturils selected from CB[5], CB[6], CB[7] and CB[8] and where n is an integer from 4 to 20.

Other cucurbiturils may be present in the composition in addition to CB[5], CB[6], CB[7] and CB[8]. For example, the composition may further comprise cucurbiturils of CB[n] where n is an integer of 4 or 9 to 20 (e.g. CB[9], CB[10], CB[11] etc.). For example the composition may further comprise, CB[4] or CB[9], or CB[4] and CB[9].

When CB[5] is present in the cucurbituril mixture, the concentration of CB[5] may be from about 0.1 to about 99% by weight, more particularly from about 0.5 to about 75% by weight, more particularly from about 1 to about 50% by weight, more particularly from about 2 to about 30% by weight, more particularly from about 5 to about 25% by weight, more particularly from about 10 to about 20% by weight, based on the total weight of the cucurbituril in the composition.

When CB[6] is present in the cucurbituril mixture, the concentration of CB[6] may be from about 0.1 to about 99% by weight, more particularly from about 1 to about 75% by weight, more particularly from about 5 to about 60% by weight, more particularly from about 20 to about 55% by weight, more particularly from about 35% by weight to about 55% by weight, based on the total weight of cucurbituril in the composition.

When CB[7] is present in the cucurbituril mixture, the concentration of CB[7] may be from about 0.1 to 99% by weight, more particularly from about 5 to about 75% by weight, more particularly from about 10 to about 60% by weight, more particularly from about 20% by weight to about 45% by weight, based on the total weight of cucurbituril in the composition. In one embodiment, the concentration of CB[7] is less than 45% by weight, based on the total weight of cucurbituril in the composition.

When CB[8] is present in the cucurbituril mixture, the concentration of CB[8] may be from about 0.1 to 99% by weight, more particularly from about 0,5 to about 75% by weight, more particularly from about 1 to about 30% by weight, more particularly about 5 to about 25% by weight, more particularly from about 10 to about 20% by weight, based on the total weight of cucurbituril in the composition.

The total concentration of the at least two different cucurbiturils selected from CB[5], CB[6], CB[7] and CB[8]

may be greater than 75% by weight, more particularly greater than about 90% by weight, more particularly greater than about 99% by weight of the total weight of cucurbituril in the composition. The remaining components of the cucurbituril mixture may contain CB[4], CB[9] and/or higher cucurbiturils (i.e. CB[10]-CB[20]), either as a single sized cucurbituril or as a mixture of these sizes.

In a particular embodiment, the cucurbituril mixture comprises between 12 and 17% by weight of CB[5]; 45 and 50% by weight of CB[6]; 22 and 27% by weight of CB[7]; 12 and 17% by weight of CB[8]; and less than 1% by weight of CB[9] and higher cucurbiturils, based on the total weight of cucurbituril in the composition.

The % weights of cucurbituril described above are based on the total weight of cucurbituril (of all sizes) in the composition. The cucurbituril mixture used as the starting material to prepare the compositions of the invention, i.e. the mixture of uncomplexed cucurbituril, will have the same weight percentages as described above.

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

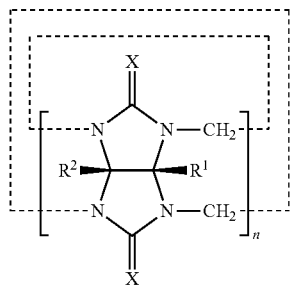

wherein:
n is an integer between 4 and 20;
and for each glycoluril unit:
each X is O, S or $NR^3$, and
—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$carboaryl, and $C_{5-20}$heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n-1 of the glycoluril units In one embodiment, n is 5, 6, 7, 8, 9, 10, 11 or 12.
In one embodiment, n is 5, 6, 7 or 8.
In one embodiment, each X is O.
In one embodiment, each X is S.
In one embodiment, $R^1$ and $R^2$ are each independently H.
In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$alkyl. The $C_{1-20}$alkyl group may be linear and/or saturated. Each group —$R^3$ may be independently unsubstituted or substituted. Preferred substituents are selected from: —$R^4$, —OH, —$OR^4$, —SH, —$SR^4$, —COON, —$COOR^4$, —$NH_2$, —$NHR^4$ and —$N(R^4)_2$, wherein —$R^4$ is selected from $C_{1-20}$alkyl, $C_{6-20}$carboaryl, and $C_{5-20}$heteroaryl. The substituents may be independently selected from —COON and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$. Each —$R^4$ is $C_{1-6}$alkyl and is itself preferably substituted.

In one embodiment, references to a cucurbituril compound are references to derivatives thereof. The cucurbiturils of the invention may be in the native form or they may be modified as described above in order to improve their solubility, dispersibility, and more generally their formulation and handling.

Complex

In one aspect the present invention provides use of a mixture of cucurbiturils having a distribution of cavity sizes, which may form complexes with malodour molecules.

The compositions described herein comprise a cucurbituril mixture wherein the cucurbiturils are substantially free of guest molecules, meaning more than 75% by weight, more particularly more than 90% by weight, still more particularly more than 95 wt % by weight of the cucurbiturils are free of guest molecules. When the compositions of the invention come in to contact with malodour molecules, the cucurbiturils form a malodour-cucurbituril complex which results in masking of the malodour.

In certain instances, the cucurbituril hosts a guest molecule, which is then released by molecular exchange when the cucurbituril complexes with a malodour molecule/component. In one embodiment, the guest molecule is a molecule which is used in household care or personal care. In particular, the guest molecule is a fragrance molecule. The guest molecule is physically bound to the cucurbituril and is released when the cucurbituril complexes with a malodour molecule. Suitable fragrance molecules are known to the skilled person and are also described in GB1602664.3 which is hereby incorporated by reference.

When forming a complex with a cucurbituril, the malodour molecule is physically bound to the cucurbituril substrate. The terms "physically bound", "physical bonding" and "physical linkage" used throughout include bonding by Van der Waals forces and other types of physical bond. In the present context, hydrogen bonds are also considered as physical bonds. Systems that are capable of establishing strong physical bonding with malodour have considerable advantages over systems relying on chemical bonding.

In particular, physical binding allows the formation of complexes with a multitude of malodours having a multitude of chemical structures and functions. Even malodour molecules that have no reactive groups can bind physically to the cucurbiturils.

The cucurbituril-malodour complex may be a ternary or a binary complex. Thus, the cucurbituril may hold one or two guest malodour molecules within its cavity. Where a cucurbituril holds two malodour molecules, the malodour molecules may be the same or they may be different. A cucurbituril that is capable of hosting two malodour molecules may also be capable of forming a stable binary complex with a single malodour. The formation of a ternary guest-host complex is believed to proceed via an intermediate binary complex.

In one embodiment, the cucurbituril is capable of forming a ternary complex. For example, CB[8] is capable of forming a ternary complex.

In one embodiment, the cucurbituril is capable of forming a binary complex. CB[8] may also form a binary complex.

In one embodiment, the cucurbituril is capable of forming ternary and binary complexes. For example, CB[8] is capable of forming a ternary or a binary complex, depending upon the nature of the guest.

The applicant has established that to perform as a malodour counteracting system, a malodour-cucurbituril complex must have a binding constant preferably larger than 100 $M^{-1}$. In one embodiment, the binding constant is at least 1000 $M^{-1}$.

The binding constant for a binary complex between a malodour M and a cucurbituril CB[x], where x is an integer from 4 to 20, is defined according to the Le Chatelier principle of mass action as:

$$M + CB[x] \rightleftarrows MCB[x]$$

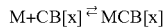

$$K = [MCB[x]]/([M]*[CB[x]])$$

where the square brackets denote the concentration of the species in mol/l.

Malodours

The term "malodour" refers to unpleasant odours which are frequently encountered in everyday life and have a variety of origins. Typical malodours include odours that emanate from uncontrolled industrial activity, from human and pet body such as perspiration and excretion, from kitchen and food processing, from tobacco smoke, and from mould. Some of the most disturbing malodour for the human being are sweat; faecal; urine; wet pet; cooking odours, especially garlic, cabbage, fish and onion; and the like. Malodours may also emanate from the fatty acid and fatty acid derivatives present in consumer products, for example in soaps, detergents, shampoos, and conditioners. Other examples of particularly undesirable malodours are those produced by depilatory creams (sulphur compounds). All of these malodours are particularly pungent.

The mixture of cucurbiturils may be used to counteract a broad range of malodour molecules.

In the context of the present invention, the term "malodour counteraction" or "malodour counteracting" is considered as equivalent to "malodour suppression", "malodour mitigation" or "malodour neutralization". The result is a significant decrease of the intensity of the malodour perception by any person exposed to the source of the malodour. The intensity of odours is generally measured by using the Labelled Magnitude Scale (LMS), a definition of which can be found in Green BG, Shaffer GS and Gilmore MM 1993, Derivation and evaluation of a semantic scale of oral sensation magnitude with apparent ratio properties, Chemical Senses. 18(6):683-702. For odours, the scale encompasses the following strength attributes: Barely Detectable, Weak, Moderate, Strong, Very Strong and Strongest Imaginable. In the context of the present invention, a "significant decrease" means that the intensity attribute of the malodour, after application of the cucurbiturils, is Weak or Barely Detectable.

Alternatively, a linear scale may be used, extending for example from 0 (no intensity perceived) and 10 (highest intensity perceived).

Odour intensity scores are preferably obtained by a panel of several people.

In the present invention, the malodour to be counteracted is a complex malodour, comprising more than one malodour component.

In one embodiment, the complex malodour comprises malodour components having a diversity of chemical functions.

CB[5] having a cavity volume of 82 Angstrom$^3$, preferably binds small gaseous malodours, such as acetylene, hydrogen sulphide and carbon disulphide.

Larger malodour molecules comprising O-, N- and S-heteroatoms preferably bind to larger cucurbiturils (e.g. CB[7] and CB[8]).

The malodour may be selected from, but not limited to:
Nitrogen- and sulphur-containing molecules, such as Allyl amine; Methyl amine; Ethyl amine; Cyclobutyl amine (cyclobutanamine, urine), Cyclopentyl amine (cyclopentanamine); Cyclohexyl amine (cyclohexanamine); Cycloheptyl amine (cyclobutanamine); Isopropylamine; Butylamine; Dibu-tylamine (N-Butyl-1-butanamin); Dimethyl ethanolamine (2-(Dimethylamino) ethanol); Methyl ethanolamine (2-(Methylamino) ethanol); Diethyl ethanolamine (2-(Diethylamino) ethanol); Diethylamine (N-methylethanamine, fishy); Dipropyl amine (N-Propyl-1-propanamine); Diiso-propylamine (N-Isopropyl-2-propanamine); Dimethyl acetamide (N,N-Dimethylacetamide); Ethyl methylamine (N-Methylethanamine); Ethyl propylamine (N-ethylpropanamide); Trimethyl amine (fishy); Triethylamine (fishy); Ethylene diamine (1,2-ethanediamine, musty ammoniacal); Propylene diamine (1,3-propanediamine); tetramethylenediamine (1,4-butanediamine, Putrescine, foul); Ethylene imine (Aziridine, ammoniacal); Morpholine (fishy); Ethyl morpholine (4-ethylmorpholine, sour); Pyrrolidine (semen); Methyl ethyl pyridine (2-Ethyl-3-methylpyridine); Pyridine (burnt, sickening); Vinyl pyridine (4-vinylpyridie, nauseating); Skatole (3-methylindole, faecal); Indole (faecal); Cadaverine (Pentane-1,5-diamine, putrid); Hydrogen sulphide (rotten egg); Allyl disulphide (3-(Allyldisulfanyl)-1-propene, garlic); Ethyl isothiocyanate (isothiocyanatoethane; pungent, mustard, garlic); Ally isothiocyanate (3-isothiocyanatoprop-1-éne, sulphurous); Allyl mercaptan (2-Propene-1-thiol, garlic, sulphurous); Allyl sulphide (3-(Allylsulfanyl)-1-propene; sulphurous); Diallyl sulphide (3-(Allylsulfanyl)-1-propene; sulphurous); Dimethyl disulphide ((methylsulfanyl)ethane, unpleasant, garlic); Dimethyl trisulphide (Dimethyltrisulfane, foul); Diethyl sulphide ((Ethylsulfanyl)ethane, sulphurous); Butyl sulphide (1-(Butylsulfanyl)butane, garlic, violet); Diethyl trisulfide (Diethyltrisulfane, foul, garlic); Ethyl methyl disulphide ((methylsulfanyl)ethane, sulphurous); Phenyl sulphide (1,1'-sulfanediyldibenzene, sulphurous); Ethyl mercaptan (1.ethanethiol, sulphurous); Amyl mercaptan (1-Pentanethiol); Isoamyl mercaptan (3-methylbutane-1-thiol; sulphurous, onion); Butyl mercaptan (1-Butanethiol, skunk-like); Isobutyl mercaptan (2-methylpropane-1-thiol, sulphurous, mustard); Dodecyl mercaptan (1-dodecanethiol); Carbon disulphide (Methanedithione, disagreeable, sweet); Dimethyl trithiocarbonate (Dimethyl carbonotrithioate); Thiophenol mercaptan;

Oxygen-containing five-member ring molecules, such as Sotolone; nor-Sotolone.

Saturated and unsaturated alkyl and hydroxyalkyl carboxylic acids, such as Acetic acid, Propionic acid, Butyric acid, iso-Valeric acid, n-Valeric acid, 2-Methyl-butyric acid, 3-Methyl-2-hexenoic acid, and 3-Methyl-3-hydroxy hexanoic acid.

Malodour Counteracting Compositions

In addition to the mixture of different sized cucurbiturils, the compositions used in the invention may also include one or more additives known to those skilled in the art.

In one embodiment, the compositions used in the present invention further comprise one or more molecules, mixtures of molecules or polymers useful in counteracting malodour, in addition to cucurbituril. Suitable molecules, mixtures of molecules or polymers useful in counteracting malodour are known to the skilled person and include other host molecules. For example, other members of the cavitand family, which includes cyclodextrin, calixarene and crown ether, could be used in combination with cucurbituril. Further suitable classes of molecules or compounds include charcoal and zinc ricinolate.

In one embodiment, the mixture of cucurbiturils, and optional additional malodour counteracting molecules, further comprises one or more additives selected from preservatives, dyes, pigments, sequestrants and antioxidants.

The cucurbituril-based compositions for use in the present invention can be provided in a multitude of forms and formats. In a particular embodiment, the mixture of cucurbiturils may be provided in powder form, in solution or as a dispersion in a liquid, in a super-critical liquid or as a compressed gas, adsorbed on a substrate, for example on a fabric, a non-woven pad, an adsorbent, and the like, or in spray form.

The mixture of cucurbiturils may also be added to a product, such as a consumer product for laundry care, home care or personal care. These consumer products may be in the form of powders or granulates, tablets or single-dose units, dispersions, emulsions, micro-emulsions or solutions, a hydro-alcoholic product, wipes or sponges, aerosols or liquid dispensers, creams, balsam, polish, waxes, and the like. Methods of incorporating the present composition into these different forms are well known to the person skilled in the art.

The consumer product may be a detergent, a cleansing composition, a shampoo, a softener, a softener sheet, a conditioner, a refresher, an air freshener, a deodorizing composition, a personal deodorant, an antiperspirant, a cosmetic product, a fine fragrance, a body mist, a candle, a hard surface cleaner, a cleansing wipe or mop, a soap, a styling gel, a humidity absorber, an air filtration device, a finishing product, a diaper or sanitary product, and the like.

The cucurbituril composition may also be used to provide malodour counteracting properties to textiles, to functional textiles and to textile finishing product; to air and various materials, such as paper, wood, plastics, stone, ceramics, metals, metal wool, wool, fibres, foams, filter material, absorbents, adsorbents, plasters, paints, inks, and the like.

The cucurbituril composition described herein may also be admixed with or incorporated into a perfume oil, before addition to a product.

If the cucurbituril composition is added to a perfume oil, the resulting mixture may then be microencapsulated by any methods known to the art, such as by spray drying, spray granulation, matrix particle formation, core-shell encapsulation, and the like.

Certain aspects and embodiments of the invention will now be illustrated by way of example.

Experimental and Results

The following Examples were all carried out at 20 +/−2 degrees centigrade.

EXAMPLE 1

Malodour-Counteracting using CB[n]

The cucurbiturils/malodour mixtures were prepared by complexing the malodour with a mixture of cucurbiturils, referred to as CB[n]. The composition of the CB[n] mixture was 15% by weight of CB[5], 48% by weight of CB[6], 25% by weight of CB[7] and 12% by weight of CB[8]. The release profile of four CB[n]/malodour mixtures was investigated using an odour characterization test. A ten member trained panel characterized the odour of such compositions in terms of preference and odour intensity (using a scale of 1 to 9). The CB[n]/malodour mixture was formulated by adding 0.4 mL of malodour solution to a glass vial containing 2.5 g of CB[n] powder. The vials were then placed in empty 500 mL flasks for odour evaluation. The odour of each CB[n]/malodour composition was then compared to the corresponding CB[n]-free malodour. The composition of malodours are as follows: fish (ammonia, triethanolamine and dimethylamine, each 1.5 weight % in ethanol solution), body odour (0.05 weight % isovaleric acid in ethanol), garlic (0.25 weight % garlic oil in ethanol), shrimp paste (0.5 weight % Thai shrimp paste in ethanol) and bathroom with % U.S. Government standard bathroom malodour). The tests were done in a humidity of 40%. The results are reported in Table 1.

Table [1] shows the capability of CB[n] to counteract malodours.

|  | Average odour intensity (Scale 1 to 9) | Panel chose as least preferred (%) |
|---|---|---|
| Bathroom malodour | 6.8 | 100 |
| Bathroom/CB[n] complex | 2.7 | 0 |
| Fish malodour | 7.6 | 100 |
| Fish/CB[n] complex | 1.7 | 0 |
| Body odour | 8.5 | 100 |
| Body odour/CB[n] complex | 3.5 | 0 |
| Garlic | 7.1 | 100 |
| Garlic/CB[n] complex | 2.5 | 0 |
| Shrimp paste | 6.4 | 89 |
| Shrimp paste P/CB[n] complex | 2.2 | 11 |

Outcome: it is apparent from the table that in the presence of CB[n], all malodours were counteracted by CB[n].

EXAMPLE 2

Fish and Bathroom Malodour-Counteracting using CB[n], Compared to Hydroxypropyl-Beta-Cyclodextrin(CD)

CB[n] and CD ability to capture fish and bathroom malodours were analysed in conditions of 40% humidity using an odour characterization test. A nine member trained panel characterized the odour of such compositions in terms of preference and odour intensity (using a scale of 1 to 9). The CB[n] and CD mixtures with malodours were formulated as follows: adding 0.4 ml of malodour solution to a glass vial containing 2.5 g of CB[n] or CD powder. The vials containing the mixtures were then placed in empty 500 mL flasks for odour evaluation. The results are reported in Table 2.

Table [2] is a table showing the advantage of using CB[n] over CD for counteracting fish and bathroom malodour in moist conditions with a humidity of 40%.

|  |  | Average odour intensity (Scale 1 to 9) | Panel chose as least preferred (%) |
|---|---|---|---|
| 40% relative humidity | Fish malodour/CD | 7.7 | 100 |
|  | Fish malodour/CB[n] | 2.6 | 0 |
|  | Bathroom malodour/CD | 6.4 | 100 |
|  | Bathroom malodour/CB[n] | 3.3 | 0 |

Outcome: it is apparent from the table that the bonding capability of CB[n] with fish odour and bathroom malodour is superior to Hydroxypropyl-beta-cyclodextrin. This translates in a better performance of CB[n] for supressing malodour.

EXAMPLE 3

Fish and Bathroom Malodour-Counteracting using CB[n], Compared to CB[7]

CB[n] and CB[7] ability to capture fish and bathroom malodours were analysed in conditions of 40% humidity using an odour characterization test. A nine member trained panel characterized the odour of such compositions in terms of preference and odour intensity (using a scale of 1 to 9). The mixtures were formulated as described in the previous example. The vials were then placed in empty 500 mL flasks with for odour evaluation. The results are reported in Table 3.

Table [3] shows the advantage of using CB[n] over CB[7] for counteracting fish and bathroom malodour.

|  |  | Average odour intensity (Scale 1 to 9) | Panel chose as least preferred (%) |
|---|---|---|---|
| 40% relative humidity | Fish malodour/CB7 | 7.4 | 100 |
|  | Fish malodour/CB[n] | 3.0 | 0 |
|  | Bathroom/CB7 | 4.7 | 29 |
|  | Bathroom/CB[n] | 5.6 | 71 |

Outcome: it is apparent from the table that the bonding capability of CB[n] is superior to CB[7]. This translates in a better performance of CB[n] for supressing both malodours.

EXAMPLE 4

Fish and Bathroom Malodour-Counteracting using CB[n], Compared to Hydroxypropyl-Beta-Cyclodextrin(CD) Under High Humidity CB[n] and CD ability to capture fish and bathroom malodours were analysed in conditions of 88% humidity using the same odour characterization test described in Examples 2 and 3. The results are reported in Table 4.

Table [4] is a table showing the advantage of using CB[n] over CD for counteracting fish and bathroom malodour in moist conditions with a humidity of 88%.

|  |  | Average odour intensity (Scale 1 to 9) | Panel chose as least preferred (%) |
|---|---|---|---|
| 88% relative humidity | Fish malodour/CD | 3.0 | 100 |
|  | Fish malodour/CB[n] | 1.0 | 0 |
|  | Bathroom malodour/CD | 5.9 | 100 |
|  | Bathroom malodour/CB[n] | 3.7 | 0 |

Outcome: it is apparent from the table that the bonding capability of CB[n] with fish odour and bathroom malodour is superior to Hydroxypropyl-beta-cyclodextrin. This translates in a better performance of CB[n] for supressing both malodours under high humidity conditions.

EXAMPLE 5

Fish and Bathroom Malodour-Counteracting using CB[n], Compared to CB[7] Under High Humidity CB[n] and CB[7] ability to capture fish and bathroom malodours were analysed in conditions of 88% humidity using the same odour characterization test described in Examples 3 and 4. The results are reported in Table 5.

Table [5] shows the advantage of using CB[n] over CB[7] for counteracting fish and bathroom malodour in moist conditions with a humidity of 88%.

|  |  | Average odour intensity (Scale 1 to 9) | Panel chose as least preferred (%) |
|---|---|---|---|
| 88% relative humidity | Fish malodour/CB7 | 7.1 | 100 |
|  | Fish malodour/CB[n] | 1.7 | 0 |
|  | Bathroom/CB7 | 3.6 | 70 |
|  | Bathroom/CB[n] | 3.2 | 30 |

Outcome: it is apparent from the table that the bonding capability of CB[n] with fish and bathroom malodours is superior to CB[7]. This translates in a better performance of CB[n] for supressing both malodours under high humidity conditions.

The invention claimed is:

1. A method for counteracting malodour in a moist environment, providing a mixture comprising 0.1-20% by weight CB[5], 35-75% by weight CB[6], 10-45% by weight CB[7] and 10-30% by weight CB[8], based on a total weight of cucurbiturils in the mixture, in powder form, adsorbed on a substrate, or in aerosol form, wherein the moist environment at the interface with the mixture is air with a relative humidity higher than 40%, and wherein formation of the aerosol form disperses the cucurbiturils into the moist environment.

2. The method according to claim 1, wherein the relative humidity of the moist environment is at least 50%.

3. The method according to claim 2, wherein the relative humidity of the moist environment is 100%.

4. The method according to claim 1, wherein the malodour is a malodour complex comprising more than one malodour component.

5. The method according to claim 1, wherein the mixture further comprises one or more CB [n], wherein n is an integer independently selected from 4 or 9-20.

6. A method for counteracting malodour in a moist environment, providing a mixture of two or more cucurbiturils comprising CB[6] and one or more cucurbiturils selected from CB[5], CB [7] and CB[8] in powder form, adsorbed on a substrate, or in aerosol form, wherein the moist environment at the interface with the mixture of two or more cucurbiturils is air with a relative humidity higher than 40%, wherein formation of the aerosol form disperses the cucurbiturils into the moist environment, and wherein the concentration of CB[6] in the mixture is from 45% to 50% by weight, based on the total weight of cucurbiturils in the mixture.

7. The method according to claim 1, wherein the total concentration of CB[5], CB[6], CB[7] and CB[8] in the mixture is greater than 75% by weight, based on the total weight of cucurbiturils in the mixture.

8. The method according to claim 1, wherein a complex of a malodour and cucurbituril has a binding constant of at least 100 $M^{-1}$.

9. The method according to claim 1, wherein a complex of a malodour and cucurbituril has a binding constant of at least 1000 $M^{-1}$.

10. The method according to claim 1, used to counteract the malodour of a nitrogen-containing molecule, a sulphur-containing molecule or an oxygen- containing molecule.

11. The method according to claim 1 for counteracting one or more malodours selected from nitrogen- and sulphur-containing molecules; allyl amine; methyl amine; ethyl amine; cyclobutyl amine, cyclopentyl amine; cyclohexyl amine; cycloheptyl amine; isopropylamine; butylamine; dibutylamine; dimethyl ethanolamine; methyl ethanolamine; diethyl ethanolamine; diethylamine; dipropyl amine; diiso-propylamine; dimethyl acetamide; ethyl methylamine; ethyl propylamine; trimethyl amine; triethylamine; ethylene diamine; propylene diamine; tetramethylenediamine; ethylene imine; morpholine; ethyl morpholine; pyrrolidine; methyl ethyl pyridine; pyridine; vinyl pyridine; skatole; indole; cadaverine; hydrogen sulphide; allyl disulphide; ethyl isothiocyanate; allyl isothiocyanate; allyl mercaptan; allyl sulphide; diallyl sulphide; dimethyl disulphide; dimethyl trisulphide; diethyl sulphide; butyl sulphide; diethyl trisulfide; ethyl methyl disulphide; phenyl sulphide; ethyl mercaptan; amyl mercaptan; isoamyl mercaptan; butyl mercaptan; isobutyl mercaptan; dodecyl mercaptan; carbon disulphide; dimethyl trithiocarbonate; thiophenol mercaptan; oxygen-containing five-member ring molecules; sotolone; nor-sotolone; saturated and unsaturated alkyl and hydroxyalkyl carboxylic acids; acetic acid; propionic acid;, butyric acid; iso-valeric acid; n-valeric acid; 2-methyl-butyric acid; 3-methyl-2-hexenoic acid; and 3- methyl-3-hydroxy hexanoic acid.

12. The method according to claim 1, wherein one or more of the cucurbiturils are complexed with a fragrance molecule, whereby the fragrance is released when the cucurbiturils complex with a malodour component.

13. A method for counteracting malodour in a moist environment, providing a mixture comprising 0.1-20% by weight CB[5], 35-75% by weight CB[6], 10-45% by weight CB[7] and 10-30% by weight CB[8], based on a total weight of cucurbiturils in the mixture, in powder form, adsorbed on a substrate, or in aerosol form, wherein the moist environment at the interface with the mixture is air with a relative humidity higher than 40%, wherein the formation of the aerosol form disperses the cucurbiturils into the moist environment, and wherein the mixture is a component of a product.

14. The method according to claim 13, wherein the product is a softener sheet, an air freshener or an air filtration device.

15. The method according to claim 1, wherein the mixture of two or more cucurbiturils is in the aerosol form, wherein the aerosol is formed such that more than 75 weight % by weight of the cucurbiturils are free of guest molecules before coming into contact with malodour molecules, and the malodour molecules are airborne; and the method further comprises masking the malodour by contacting the airborne malodour molecules with the cucurbiturils of the aerosol to form a malodour-cucurbituril complex.

16. The method according to claim 1, wherein the substrate is a fabric, a non-woven pad, or an adsorbent.

17. The method according to claim 1 for counteracting one or more malodours selected from urine, fishy, musty, ammoniacal, fecal, semen, rotten egg, putrid, garlic, mustard, sulphurous, onion, skunk-like, and sweet.

* * * * *